US006491901B2

(12) United States Patent
Gers-Barlag et al.

(10) Patent No.: US 6,491,901 B2
(45) Date of Patent: Dec. 10, 2002

(54) STABILIZATION OF OXIDATION- AND/OR UV-SENSITIVE ACTIVE INGREDIENTS

(75) Inventors: Heinrich Gers-Barlag, Kummerfeld (DE); Volker Wendel, Hamburg (DE); Wiebke Grundt, Buchholz (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/789,245

(22) Filed: Feb. 20, 2001

(65) Prior Publication Data

US 2001/0022966 A1 Sep. 20, 2001

(30) Foreign Application Priority Data

Feb. 25, 2000 (DE) .......................................... 100 08 895

(51) Int. Cl.$^7$ ................................................. A61K 7/42
(52) U.S. Cl. ......................................... 424/59; 424/401
(58) Field of Search ..................................... 424/401, 59

(56) References Cited

U.S. PATENT DOCUMENTS 5,191,121 A    3/1993  Yamada et al. ............. 564/305
5,549,659 A    8/1996  Rinaldi et al. ................ 424/59
5,993,789 A   11/1999  Bonda et al. ................. 424/59
6,126,925 A * 10/2000  Bonda et al. ................. 424/59

FOREIGN PATENT DOCUMENTS

EP    0 514 491         11/1992
FR    2 801 210 A1      5/2001

OTHER PUBLICATIONS

Bonda, Craig et al., "A New Photostabilizer for Full Spectrum Sunscreens", Allured's Cosmetics and Toiletries, vol. 115, No. 6, Jun. 2000, pp. 37–45.

* cited by examiner

Primary Examiner—Jose' G. Dees
Assistant Examiner—Konata M. George
(74) Attorney, Agent, or Firm—Norris McLaughlin & Marcus

(57) ABSTRACT

Synergistic combinations and cosmetic or dermatological formulations comprising same.

4 Claims, No Drawings

STABILIZATION OF OXIDATION- AND/OR UV-SENSITIVE ACTIVE INGREDIENTS

STABILIZATION OF OXIDATION- AND/OR UV-SENSITIVE ACTIVE INGREDIENTS

The present invention relates to combinations for the stabilization of oxidation-sensitive and/or UV-sensitive active ingredients, and to cosmetic and dermatological formulations containing oxidation-sensitive and/or UV-sensitive active ingredients stabilized in this way. In particular, it relates to cosmetic and dermatological light protection formulations and to formulations containing UV-sensitive light protection filter substances which are stabilized by the use of these combinations.

The harmful effect of the ultraviolet part of solar radiation on the skin is generally known. Depending on their respective wavelength, the rays have different effects on the skin organ: So-called UV-C radiation with a wavelength of less than 290 nm is absorbed by the ozone layer in the earth's atmosphere and is therefore of no physiological importance. By contrast, rays in the range between 290 nm and 320 nm, the so-called UV-B region, cause erythema, simple sunburn or even burns of varying severity. A maximum erythema activity of sunlight is given as the narrower region around 308 nm.

To protect against UV-B radiation, numerous compounds are known; these are mostly derivatives of 3-benzylidenecamphor, of 4-aminobenzoic acid, of cinnamic acid, of salicylic acid, of benzophenone, and also 2-phenylbenzimidazole.

An advantageous light protection filter substance is, for example, 2-ethylhexyl p-methoxycinnamate (4-methoxycinnamic 2'-ethylhexyl ester), which is available from Givaudan under the name Parsol® MCX and which is characterized by the following structure:

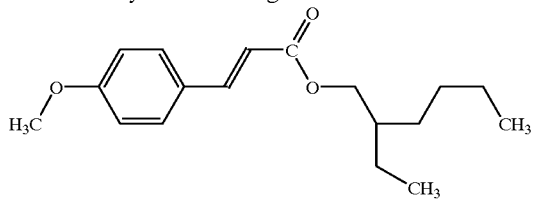

The main disadvantage of 2-ethylhexyl p-methoxycinnamate is a certain instability toward UV radiation, meaning that preparations with a content of this substance should automatically also contain certain UV stabilizers.

For a long time it has incorrectly been assumed that the long-wave UV-A radiation with a wavelength between 320 nm and 400 nm has only a negligible biological action and that, accordingly, the UV-B rays are responsible for most photodamage to the human skin. However, in the mean time numerous studies have shown that UV-A radiation is much more harmful than UV-B radiation with regard to the triggering of photodynamic, specifically phototoxic, reactions and chronic changes in the skin. The harmful effect of UV-B radiation can also be further intensified by UV-A radiation.

Thus, it has, inter alia, been proven that even UV-A radiation under quite normal every day conditions is sufficient to damage within a short period the collagen and elastin fibers which are of essential importance for the structure and strength of the skin. This results in chronic light-induced changes in the skin—the skin "ages" prematurely. The clinical manifestation of light-aged skin includes, for example, wrinkles and lines, and also an irregular, furrowed relief. In addition, the areas affected by light-induced skin aging may have irregular pigmentation. The formation of brown spots, keratoses and even carcinomas or malignant melanomas is also possible. Skin which has been aged prematurely as a result of every day UV stress is further characterized by a lower activity of the Langerhans' cells and slight, chronic inflammation.

Approximately 90% of the ultraviolet radiation which reaches the earth consists of UV-A rays. While the UV-B radiation varies widely depending on numerous factors (e.g. time of year and day or degree of latitude), the UV-A radiation remains relatively constant day after day irrespective of the time of year and day or geographical factors. At the same time, the majority of the UV-A radiation penetrates into the living epidermis, while about 70% of the UV-B rays are retained by the horny layer.

Preventive protection against UV-A rays, for example by applying light protection filter substances in the form of a cosmetic or dermatological formulation to the skin, is therefore of fundamental importance.

Known and advantageous light protection filter substances which, in particular, also offer protection against UV-A radiation are dibenzoylmethane derivatives, in particular 4-(tert-butyl)-4'-methoxydibenzoylmethane, which is characterized by the structure

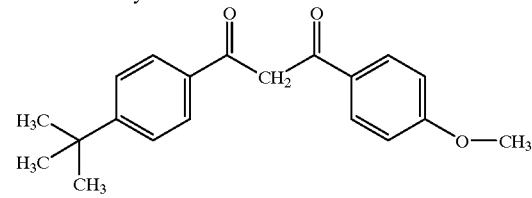

and is sold by Givaudan under the name Parsol® 1789.

The main disadvantage of this substance too is a certain instability towards UV radiation. The photochemical decomposition of all dibenzoylmethane derivatives which absorb in the UV rays follows a Norrish type I acyl cleavage. This is illustrated in the reaction scheme below using the example of 4-(tert-butyl)-4'-methoxydibenzoylmethane:

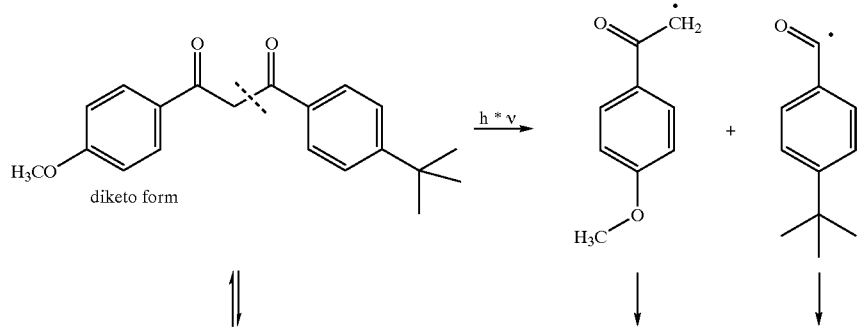

-continued

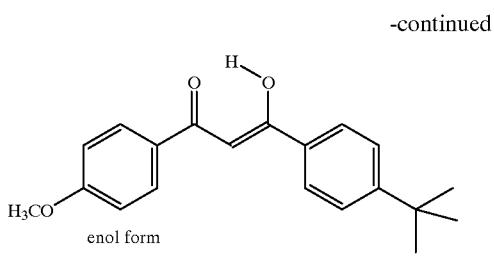
enol form

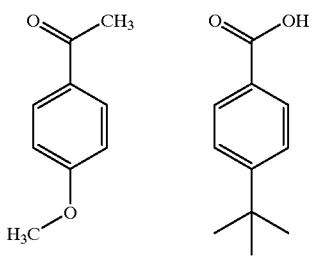

In principle, what has already been said applies for mixtures of these cinnamates and dibenzoylmethanes already mentioned. In contrast to some light protection filter combinations which are characterized by increased stability toward the respective individual substances, for mixtures of cinnamates and dibenzoylmethanes, an even stronger destabilization toward UV-light is generally observed than for the respective individual substances. This is the case in particular for mixtures of 2-ethylhexyl p-methoxycinnamate and 4-(tert-butyl)-4'-methoxydibenzoylmethane. With some certainty, these two components react under the effect of UV to give inactive products and are therefore no longer available for the UV absorption.

Possible solutions to this problem which have been proposed at different times are to protect the active ingredients from degradation by the addition of one or more stabilizers, e.g. antioxidants, or to use them in the form of more stable derivatives.

2-Ethylhexyl 2-cyano-3,3-diphenylacrylate (INCI: Octocrylene)—a UV filter substance liquid at room temperature—is also said to have a stabilizing effect on 4-(tert-butyl)-4'-methoxydibenzoylmethane. 2-Ethylhexyl 2-cyano-3,3-diphenylacrylate is characterized by the following structure:

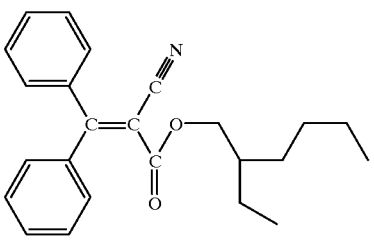

and is available, for example, from BASF under the name Uvinul® N 539.

A similar effect has also already been described for diethylhexyl naphthalate, which is given by the structural formula

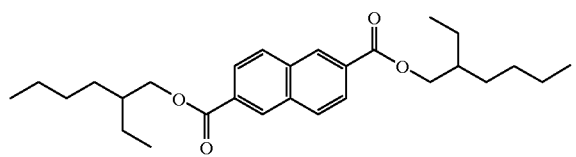

However, in all cases the effect achieved falls a long way short of that which is desired.

The prior art was unable to give any indications which would have permitted inferences to the preparations according to the invention.

The object of the present invention was to overcome the disadvantages of the prior art and to increase the stability of oxidation-sensitive and/or UV-sensitive light protection filter substances, and to provide stable preparations containing oxidation-sensitive and/or UV-sensitive light protection filter substances, the effectiveness of which is retained over a long period.

It was surprising and could in no way have been foreseen by the person skilled in the art that
  synergistic combinations of
    a) 2-ethylhexyl 2-cyano-3,3-diphenylacrylate with
    b) one or more dialkyl naphthalates
would overcome the disadvantages of the prior art.

The combinations according to the invention surprisingly have a synergistic action, i.e. have a superadditive action with regard to the individual components. By combining the individual substances according to the invention, the oxidation- and/or UV-sensitive light protection filter substance(s), in particular in cosmetic or dermatological formulations, is/are protected in an excellent manner against UV-radiation-induced decomposition. This applies in particular for dibenzoylmethane derivatives.

Of the dibenzoylmethane derivatives, 5-isopropyidibenzoylmethane (CAS No. 63250-25-9)

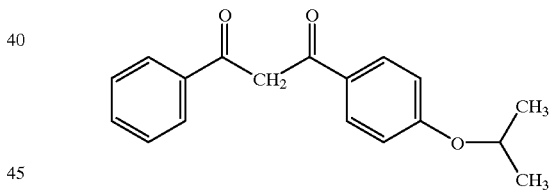

and 4-(tert-butyl)-4'-methoxydibenzoylmethane (CAS No. 70356-09-1)

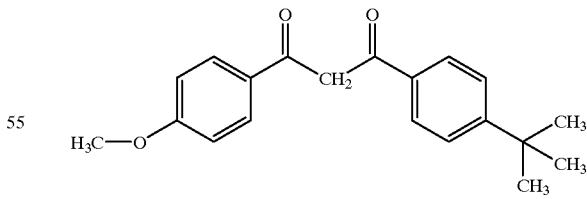

are advantageously used.

By following the teaching according to the invention, light protection preparations are obtainable which have higher stability, in particular stability toward decomposition under the effect of light, very particularly UV light, than the prior art would have suggested. In particular, the stability of 4-(tert-butyl)-4'-methoxydibenzoylmethane toward the decomposition and UV light is drastically increased. It was very particularly surprising that the increase in the stability of dibenzoylmethanes, in particular of 4-(tert-butyl)-4'-methoxydibenzoylmethane takes place to the same degree whether they are dissolved in polar or nonpolar oils components.

It was also surprising that mixtures of cinnamates and dibenzoylmethanes, in particular mixtures of 2-ethylhexyl p-methoxycinnamate and 4-(tert-butyl)-4'-methoxydibenzoylmethane, are also protected against destabilization by UV light in an excellent manner by the combination according to the invention.

The total amount of dibenzoylmethanes, in particular 4-(tert-butyl)-4'-methoxydibenzoylmethane in the finished cosmetic or dermatological preparations is advantageously chosen from the range 0.1 to 10.0% by weight, preferably 0.5 to 6.0% by weight, based on the total weight of the preparations.

Dialkyl naphthalates according to the invention are characterized by the following structure:

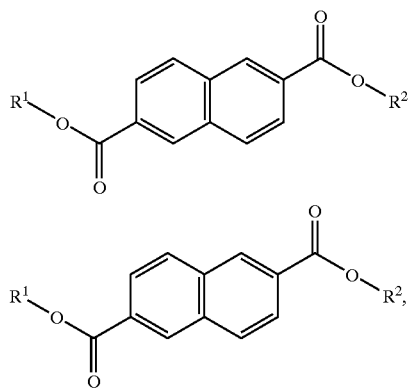

in which $R^1$ and $R^2$ independently of one another are chosen from the group of branched and unbranched alkyl groups having 6 to 24 carbon atoms.

For the purposes of the present invention, preferred dialkyl naphthalates are those for which $R^1$ and/or $R^2$ are branched alkyl groups having 6 to 10 carbon atoms. Very particular preference is given to the combination with diethylhexyl naphthalate.

The total amount of dialkyl naphthalates, in particular diethylhexyl naphthalate, in the finished cosmetic or dermatological preparations is advantageously chosen from the range 4 to 16% by weight, preferably 6 to 14% by weight, particularly preferably 6 to 10% by weight, in each case based on the total weight of the preparations.

The combinations according to the invention can advantageously be used in cosmetic and/or dermatological formulations, which may have the customary composition and serve for cosmetic and/or dermatological light protection, and also for the treatment, care and cleansing of the skin and/or of hair and as a make-up product in decorative cosmetics.

For the purposes of the present invention, it is advantageous if the content of 2-ethylhexyl 2-cyano-3,3-diphenylacrylate in the finished cosmetic or dermatological preparations is chosen to be less than 1% by weight, based on the total weight of these preparations.

It is likewise advantageous to choose the ratio of 2-ethylhexyl 2-cyano-3,3-diphenylacrylate to the oxidation- and/or UV-sensitive light protection filter substance(s) from the range 1:1 to 0.1:1, where the content of 2-ethylhexyl 2-cyano-3,3-diphenylacrylate in the finished cosmetic or dermatological preparations can also be chosen to be greater than 1% by weight, based on the total weight of these preparations.

Cosmetic and dermatological preparations which comprise the combinations according to the invention can be in a variety of forms. For example, they can be a solution, a O/W emulsion or O/W microemulsion, a W/O emulsion or W/O microemulsion, a Pickering emulsion, a multiple emulsion (e.g. a W/O/W emulsion), a sprayable emulsion, a hydrodispersion, an aerosol, a foam and also a stick.

For use, the cosmetic and dermatological preparations are applied to the skin and/or the hair in a sufficient amount in the manner customary for cosmetics.

Those cosmetic and dermatological preparations which are in the form of a sunscreen are also favorable. As well as comprising the combinations according to the invention, these preferably additionally comprise at least one further UV-A filter substance and/or at least one UV-B filter substance. Such formulations may, although not necessarily, optionally also comprise one or more inorganic pigments as UV filter substances.

Preference is given to inorganic pigments based on metal oxides and/or other metal compounds which are insoluble, or virtually insoluble, in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides.

An additional content of titanium dioxide and/or zinc oxide particles which have a stabilizing action may of course be advantageous, but is not necessary for the purposes of the present invention.

For the purposes of the present invention, it is also advantageous to provide cosmetic and dermatological preparations whose main purpose is not protection against sunlight, but which nevertheless have a content of UV protection substances. Thus, UV-A and UV-B filter substances are usually incorporated, for example, into day creams.

UV protection substances, like antioxidants and, if desired, preservatives, also represent effective protection of the preparations themselves against spoilage.

Preparations comprising the combination according to the invention also advantageously comprise substances which absorb UV radiation in the UV-A and/or UV-B region, where the total amount of the filter substances is, for example, 0.1% by weight to 30% by weight, preferably 0.5 to 20% by weight, in particular 1.0 to 15.0% by weight, based on the total weight of the preparations, in order to provide cosmetic preparations which protect the hair or the skin from the entire range of ultraviolet radiations. They can also be used as sunscreens for the hair or the skin.

Advantageous further UV-A filter substances for the purposes of the present invention are phenylene-1,4-bis(2-benzimidazyl)-3,3'-5,5'-tetrasulfonic acid:

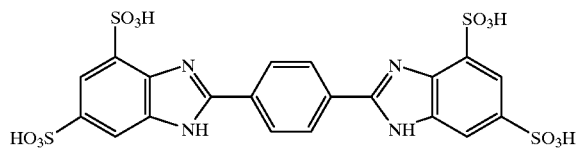

and its salts, particularly the corresponding sodium, potassium or triethanolammonium salts, in particular the phenylene-1,4-bis(2-benzimidazyl)-3,3'-5,5'-tetrasulfonic acid bis-sodium salt:

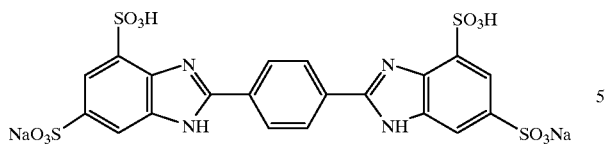

and 1,4-di(2-oxo-10-sulfo-3-bornylidenemethyl)benzene and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid) and is characterized by the following structure:

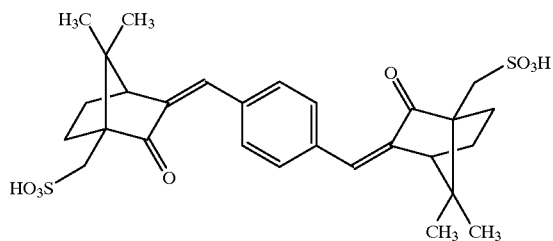

Advantageous UV filter substances for the purposes of the present invention are also broad-band filters, i.e. filter substances which absorb both UV-A and also UV-B radiation.

Advantageous broad-band filters or UV-B filter substances are, for example, bisresorcinyltriazine derivatives having the following structure:

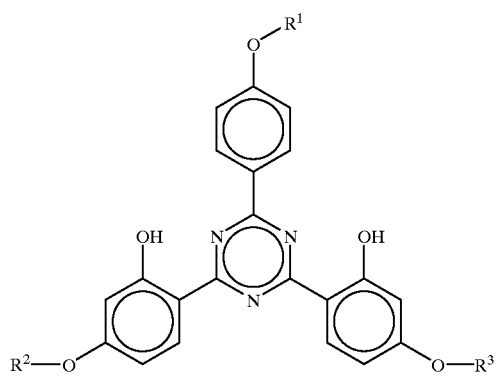

where $R^1$, $R^2$ and $R^3$ independently of one another are chosen from the group of branched and unbranched alkyl groups having 1 to 10 carbon atoms, or represent an individual hydrogen atom. Particular preference is given to 2,4-bis{[4-(2-ethylhexyloxy)-2-hydroxy]phenyl}-6-(4-methoxyphenyl)-1,3,5-triazine (INCI: Aniso Triazine), which is available under the tradename Tinosorb® S from CIBA-Chemikalien GmbH, and tris(2-ethylhexyl) 4,4',4"-(1,3,5-triazine-2,4,6-triyltriimino)trisbenzoate, synonym: 2,4,6-tris[anilino(p-carbo-2'-ethyl-1'-hexyloxy)]-1,3,5-triazine (INCI: Octyl Triazone), which is sold by BASF Aktiengesellschaft under the tradename UVINUL® T 150.

Other UV filter substances which have the structural formula

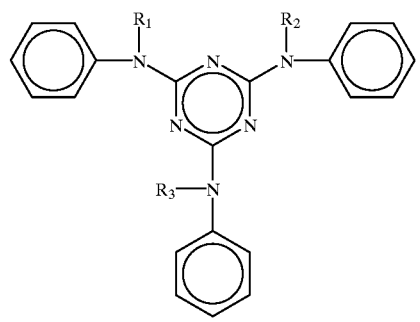

are also advantageous UV filter substances for the purposes of the present invention, for example the s-triazine derivatives described in European Laid-Open Specification EP 570 838 A1, the chemical structure of which is given by the generic formula

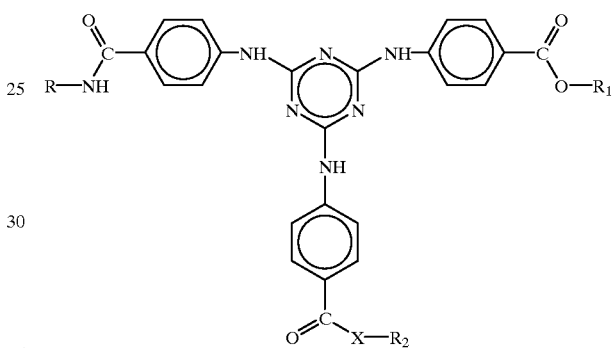

where

R is a branched or unbranched $C_1$–$C_{18}$-alkyl radical, a $C_5$–$C_{12}$-cycloalkyl radical, optionally substituted by one or more $C_1$–$C_4$-alkyl groups, X is an oxygen atom or an NH group, $R_1$ is a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

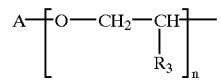

in which

A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, $R_2$ is a branched or unbranched $C_1$–$C_{18}$-alkyl radical, a $C_5$–$C_{12}$-cycloalkyl radical, optionally substituted by one or more $C_1$–$C_4$-alkyl groups, if X is the NH group, and a branched or unbranched $C_1$–$C_{18}$-alkyl radical, a $C_5$–$C_{12}$-cycloalkyl radical, optionally substituted by one or more $C_1$–$C_4$-alkyl groups, or a hydrogen atom, an alkali metal atom, an ammonium group or a group of the formula

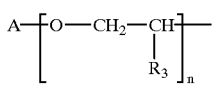

in which

A is a branched or unbranched $C_1$–$C_{18}$-alkyl radical, a $C_5$–$C_{12}$-cycloalkyl or aryl radical, optionally substituted by one or more $C_1$–$C_4$-alkyl groups, $R_3$ is a hydrogen atom or a methyl group, n is a number from 1 to 10, if X is an oxygen atom.

A particularly preferred UV filter substance for the purposes of the present invention is also an asymmetrically substituted s-triazine, the chemical structure of which is given by the formula

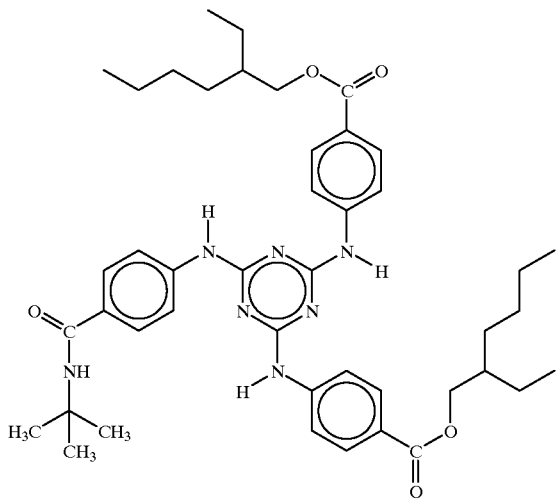

which is also referred to below as Dioctylbutylamidotriazone (INCI) and is available under the tradename UVASORB HEB from Sigma 3V.

Also in European Laid-Open Specification 775 698 preferred bisresorcinyltriazine derivatives are described, the chemical structure of which is given by the generic formula

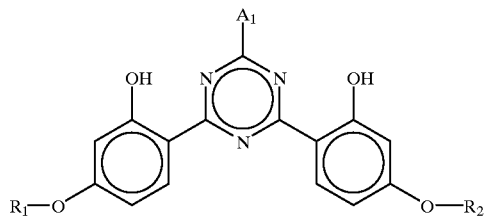

where $R_1$, $R_2$ and $A_1$ represent very different organic radicals.

Also advantageous for the purposes of the present invention are 2,4-bis{[4-(3-sulfonato)-2-hydroxypropyloxy)-2-hydroxy]phenyl}-6-(4-methoxyphenyl)-1,3,5-triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy)-2-hydroxy]phenyl}-6-[4-(2-methoxyethylcarboxy)phenylamino]-1,3,5-triazine, 2,4-bis{[4-(3-(2-propyloxy)-2-hydroxypropyloxy)-2-hydroxy]phenyl}-6-[4-(2-ethylcarboxy)phenylamino]-1,3,5-triazine, 2,4-bis{[4-(2-ethyl-hexyloxy)-2-hydroxy]phenyl}-6-(1-methylpyrrol-2-yl)-1,3,5-triazine, 2,4-bis{[4-tris(trimethylsiloxysilylpropyloxy)-2-hydroxy]phenyl}-6-(4-methoxyphenyl)-1,3,5-triazine, 2,4-bis-{[4-(2"-methylpropenyloxy)-2-hydroxy]phenyl}-6-(4-methoxyphenyl)-1,3,5-triazine and 2,4-bis{[4-(1',1',1',3',5',5',5'-heptamethylsiloxy-2"-methylpropyloxy)-2-hydroxy]phenyl}-6-(4-methoxyphenyl)-1,3,5-triazine.

An advantageous broad-band filter for the purposes of the present invention is 2,2'-methylenebis(6-(2H-benzotriazol-2-yl)-4-(1,1,3,3-tetramethylbutyl)phenol), which is characterized by the chemical structural formula

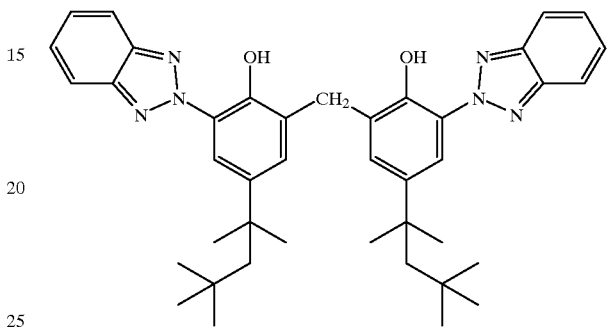

and is available under the tradename Tinosorb® M from CIBA-Chemikalien GmbH.

A further advantageous broad-band filter for the purposes of the present invention is 2-(2H-benzotriazol-2-yl)-4-methyl-6-[2-methyl-3-[1,3,3,3-tetramethyl-1-[(trimethylsilyl)-oxy]disiloxanyl]propyl]phenol (CAS No.: 155633-54-8) with the INCI name Drometrizole Trisiloxane, which is characterized by the chemical structural formula

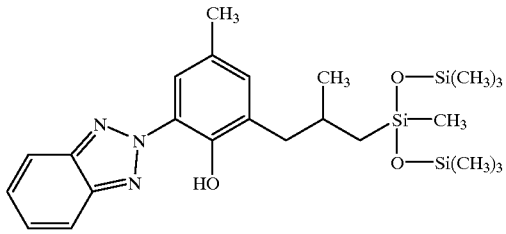

The UV-B filters may be oil-soluble or water-soluble. Advantageous oil-soluble UV-B filter substances are, for example:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

2,4,6-trianilino(p-carbo-2'-ethyl-1'-hexyloxy)-1,3,5-triazine;

esters of benzalmalonic acid, preferably di(2-ethylhexyl) 4-methoxybenzalmalonate;

esters of cinnamic acid, preferably 2-ethylhexyl 4-methoxycinnamate, isopentyl 4-methoxycinnamate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bonded to polymers.

Examples of advantageous water-soluble UV-B filter substances are:

salts of 2-phenylbenzimidazol-5-sulfonic acid, such as its sodium, potassium or its triethanolammonium salts, and also the sulfonic acid itself;

sulfonic acid derivatives of 3-benzylidenecamphor, such as, for example, 4-(2-oxo-3-bornylidenemethyl) benzenesulfonic acid, 2-methyl-5-(2-oxo-3-bornylidenemethyl)-sulfonic acid and salts thereof.

It may also be of considerable advantage to use polymer-bonded or polymeric UV filter substances in preparations according to the present invention, particularly those described in WO-A-92/20690.

In some instances, it may also be advantageous to incorporate further UV-A and/or UV-B filters in accordance with the invention into cosmetic or dermatological preparations, for example certain salicylic acid derivatives, such as 4-isopropylbenzyl salicylate, 2-ethylhexyl salicylate (=octyl salicylate), homomenthyl salicylate.

The list of said UV filters which may be used for the purposes of the present invention is not of course intended to be limiting.

The cosmetic and dermatological preparations comprising the combination according to the invention can also comprise cosmetic auxiliaries, as are customarily used in such preparations, e.g. preservatives, bactericides, perfumes, antifoams, dyes, pigments which have a coloring action, thickeners, moisturizers and/or humectants, fats, oils, waxes or other customary constituents of a cosmetic or dermatological formulation, such as alcohols, polyols, polymers, foam stabilizers, electrolytes, organic solvents or silicone derivatives.

The amounts of cosmetic or dermatological auxiliaries and/or carriers and perfume to be used in each case can, depending on the nature of the respective product, be readily determined by the person skilled in the art by simple trial and error.

According to the invention, the preparations advantageously comprise one or more antioxidants. Favorable, but nevertheless optional, antioxidants which can be used are all antioxidants which are suitable or customary for cosmetic and/or dermatological applications. In this connection, it is advantageous to use antioxidants from a single class of active ingredients if, for example, a cosmetic or dermatological application is at the fore, such as, for example, the control of oxidative stress of the skin. It is, however, also favorable to provide the preparations with a content of one or more antioxidants if the intention is for the preparations to have another purpose, e.g. as sunscreens.

The antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopine) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), and the derivatives (salts, esters, ethers, sugars, nucleotides, nucleosides, peptides and lipids) of said active ingredients which are suitable according to the invention.

The amount of the abovementioned antioxidants (one or more compounds) in the preparations according to the invention is preferably 0.001 to 30% by weight, particularly preferably 0.05 to 20% by weight, in particular 0.1 to 10% by weight, based on the total weight of the preparation.

If vitamin E and/or derivatives thereof are the antioxidant(s), it is advantageous to choose the respective concentrations thereof from the range 0.001 to 10% by weight, based on the total weight of the formulation.

If vitamin A or vitamin A derivatives, or carotenes or derivatives thereof are the antioxidant(s), it is advantageous to choose the respective concentrations thereof from the range 0.001 to 10% by weight, based on the total weight of the formulation.

The oil phase of the formulations which comprise the combination according to the invention is advantageously chosen from the group of polar oils, for example from the group of lecithins and fatty acid triglycerides, namely the triglycerol esters of saturated and/or unsaturated, branched and/or unbranched alkanecarboxylic acids having a chain length of from 8 to 24, in particular 12 to 18, carbon atoms. The fatty acid triglycerides can, for example, be advantageously chosen from the group of synthetic, semisynthetic and natural oils, such as, for example, caprylic/capric triglyceride, cocoglyceride, olive oil, sunflower oil, soybean oil, groundnut oil, rapeseed oil, almond oil, palm oil, coconut oil, castor oil, wheatgerm oil, grapeseed oil, thistle oil, evening primrose oil, macadamia nut oil and the like.

For the purposes of the present invention, further advantageous polar oil components can also be chosen from the group of esters of saturated and/or unsaturated, branched and/or unbranched alkanecarboxylic acids having a chain length of from 3 to 30 carbon atoms and saturated and/or unsaturated, branched and/or unbranched alcohols having a chain length of from 3 to 30 carbon atoms, and also from the group of esters of aromatic carboxylic acids and saturated and/or unsaturated, branched and/or unbranched alcohols having a chain length of from 3 to 30 carbon atoms. Such ester oils can then advantageously be chosen from the group octyl palmitate, octyl cocoate, octyl isostearate, octyldodecyl myristate, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and also synthetic, semisynthetic and natural mixtures of such esters, such as, for example, jojoba oil.

The oil phase can also advantageously be chosen from the group of dialkyl ethers, an advantageous example being dicaprylyl ether.

It is also preferred to choose the oil component(s) from the group isoeicosane, neopentyl glycol diheptanoate, propylene glycol dicaprylate/dicaprate, caprylic/capric/diglyceryl succinate, butylene glycol caprylate/caprate, $C_{12\text{-}13}$-alkyl lactate, di-$C_{12/13}$-alkyl tartrate, triisostearin, dipentaerythrityl hexacaprylate/hexacaprate, propylene glycol monoisostearate, tricaprylin, dimethyl isosorbide. It is particularly advantageous if the oil phase of the formulations according to the invention has a content of $C_{12\text{-}15}$-alkylbenzoate or consists entirely of this.

Any mixtures of such oil and wax components can also be used advantageously for the purposes of the present invention.

In addition, the oil phase can likewise advantageously also comprise nonpolar oils, for example those chosen from the group of branched and unbranched hydrocarbons and hydrocarbon waxes, in particular mineral oil, vaseline (petrolatum), paraffin oil, squalane and squalene, polyolefins, hydrogenated polyisobutenes and isohexadecane. Of the polyolefins, polydecenes are the preferred substances.

The oil phase can also advantageously have a content of cyclic or linear silicone oils or consist entirely of such oils, although it is preferred to use an additional content of other oil phase components apart from the silicone oil or the silicone oils.

Cyclomethicone (octamethylcyclotetrasiloxane) is advantageously used as the silicone oil to be used according to the invention. However, other silicone oils can also advantageously be used for the purposes of the present invention, for example cetyldimethicone, hexamethylcyclotrisiloxane, polydimethylsiloxane, poly(methylphenylsiloxane).

Also advantageous according to the invention are, for example, natural waxes of animal and vegetable origin, such as, for example, beeswax, chinese wax, bumble-bee wax and other insect waxes, and also shea butter.

The aqueous phase of the preparations comprising the combination according to the invention may advantageously comprise: alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and also alcohols of low carbon number, e.g. ethanol, isopropanol, 1,2-propanediol, glycerol, and, in particular, one or more thickeners, which can advantageously be chosen from the group silicon dioxide, aluminum silicates, polysaccharides or derivatives thereof, e.g. hyaluronic acid, xanthan gum, hydroxypropylmethylcellulose, particularly advantageously from the group of polyacrylates, preferably a polyacrylate from the group of so-called Carbopols, for example Carbopol grades 980, 981, 1382, 2984, 5984, in each case individually or in combination.

The examples below serve to illustrate the present invention without limiting it. The numerical values in the examples are percentages by weight, based on the total weight of the respective preparations.

EXAMPLES

| | Example 1 O/W | Example 2 O/W 1 | Example 3 O/W 2 |
|---|---|---|---|
| Stearic acid | 1.50 | — | — |
| Glycerol monostearate | 3.00 | — | — |
| Sorbitan stearate | — | 2.00 | 3.00 |
| Polyglyceryl-3 methylglucose distearate | — | 4.00 | 1.50 |
| Caprylic/capric triglyceride | — | 5.00 | — |
| Octyldodecanol | — | 5.00 | — |
| Dicaprylyl ether | — | 5.00 | — |
| Dimethicone | 2.00 | — | — |
| Phenyltrimethicone | 2.00 | — | — |
| Vitamin E acetate | 0.50 | — | 0.50 |
| Dioctylbutamidotriazone | 3.00 | — | — |
| Anisotriazine | — | — | 3.00 |
| Octocrylene | 1.50 | 1.90 | 2.90 |
| Octyl salicylate | 5.00 | — | — |
| Octyltriazone | — | 2.00 | — |
| Methylbenzylidenecamphor | — | — | 4.00 |
| Butylmethoxydibenzoylmethane | 2.00 | 2.00 | 3.00 |
| Eusolex T2000 ®[1] | 1.00 | — | — |
| Hallbrite TQ ®[2] | 4.00 | 8.00 | 7.00 |
| Preservative | 0.50 | 0.50 | 0.50 |
| Glycerol | 3.00 | 3.00 | 10.00 |
| Xanthan gum | 0.30 | 0.50 | — |
| Pemulen TR1 ® | — | — | 0.10 |
| Phenylbenzimidazolesulfonic acid | — | 2.00 | 2.00 |
| Sodium hydroxide solution 45% | 0.50 | — | 1.20 |
| Water | ad 100.00 | ad 100.00 | ad 100.00 |

[1] titanium dioxide pigments coated with simethicones and alumina
[2] diethylhexyl naphthalate

| | Example 4 W/O 1 | Example 5 W/O 2 | Example 6 W/O 3 |
|---|---|---|---|
| Polyglyceryl-2 dipolyhydroxystearate | 5.00 | — | — |
| Cetyldimethicone copolyol | — | — | 5.00 |
| PEG-30 dipolyhydroxystearate | — | 4.00 | — |
| Dimethicone | 2.00 | — | 5.00 |
| Phenyltrimethicone | — | 5.00 | 3.00 |
| Vitamin E acetate | — | 0.50 | — |
| Dioctylbutamidotriazone | 3.00 | — | 5.00 |
| Anisotriazine | 2.00 | 5.00 | 2.00 |
| Octocrylene | 3.50 | 1.90 | 1.00 |
| Octyl salicylate | 5.00 | — | 5.00 |
| Octyl methoxycinnamate | 8.00 | 10.00 | 10.00 |
| Octyltriazone | 2.00 | — | 1.00 |
| Methylbenzylidenecamphor | — | — | 4.00 |
| Butylmethoxydibenzoylmethane | 4.00 | 2.00 | — |
| Eusolex T2000 ®[1] | — | — | 2.00 |
| Aerosil R972 ®[2] | — | 0.50 | — |
| Hallbrite TQ ®[3] | 5.00 | 4.00 | 6.00 |
| Preservative | 0.50 | 0.50 | 0.50 |
| Glycerol | 5.00 | 10.00 | 5.00 |
| MgSO$_4$ | 1.00 | 1.00 | — |
| NaCl | — | — | 1.00 |
| Phenylbenzimidazolesulfonic acid | — | — | 4.00 |
| Sodium hydroxide solution 45% | — | — | 1.30 |
| Water | ad 100.00 | ad 100.00 | ad 100.00 |

[1] titanium dioxide pigments coated with simethicones and alumina
[2] silicon dioxide particles with water-repellent coating
[3] diethylhexyl naphthalate

| | Example 7 W/O Pickering emulsion | Example 8 Spray | Example 9 Spray |
|---|---|---|---|
| Glycerol monostearate | — | 4.00 | — |
| Glycerol monostearate SE | — | — | 4.50 |

-continued

| | Example 7 W/O Pickering emulsion | Example 8 Spray | Example 9 Spray |
|---|---|---|---|
| Ceteareth-20 | — | — | 1.00 |
| Ceteareth-12 | — | 1.50 | — |
| Dimethicone | — | — | 2.00 |
| Phenyltrimethicone | 5.00 | — | — |
| Vitamin E acetate | 0.50 | — | — |
| Dioctylbutamidotriazone | 5.00 | — | 2.00 |
| Anisotriazine | 5.00 | 2.00 | — |
| Octocrylene | 2.90 | 2.90 | 1.50 |
| Octyl salicylate | 5.00 | — | 2.00 |
| Octyl methoxycinnamate | 10.00 | 5.00 | — |
| Octyltriazone | — | 1.00 | — |
| Butylmethoxydibenzoylmethane | 3.00 | 3.00 | 2.00 |
| Eusolex T2000 ®[1] | 5.00 | — | — |
| Aerosil R972 ®[2] | 1.00 | — | — |
| Hallbrite TQ ®[3] | 6.00 | 4.00 | 4.00 |
| Preservative | 0.50 | 0.50 | 0.50 |
| Glycerol | 3.00 | 10.00 | 5.00 |
| Phenylbenzimidazolesulfonic acid | — | 1.00 | — |
| Sodium hydroxide solution 45% | — | 0.40 | — |
| Water | ad 100 | ad 100 | ad 100 |

[1]titanium dioxide pigments coated with simethicones and alumina
[2]silicon dioxide particles with water-repellent coating
[3]diethylhexyl naphthalate

What is claimed is:

1. A cosmetic or dermatological formulation comprising an oxidation-and/or UV-sensitive light protection filter substance chosen from the group consisting of one or both in combination of 4-(tert-butyl)-4'-methoxydibenzoylmethane and ethylhexyl p-methoxycinnamate, and a stabilizing formulation comprising a synergistic combination of 2-ethylhexyl 2-cyano-3,3-diphenylacrylate and one or more dialkyl naphthalates, wherein the 2-ethylhexyl 2-cyano-3,3-diphenylacrylate and the dialkyl naphthalates are present in a ratio of their respective weight percentages in the total formulation, of between about 0.03 to about 0.9 and the 2-ethylhexyl 2-cyano-3,3-diphenylacrylate comprises less than 3.5% of the formulation.

2. A method of stabilizing a cosmetic or dermatological formulation comprising an oxidation- and/or UV-sensitive light protection filter substance chosen from the group consisting of one or both in combination of 4-(tert-butyl)-4'-methoxydibenzoylmethane and ethylhexyl p-methoxycinnamate, comprising the step of
adding a stabilizing formulation comprising a synergistic combination of 2-ethylhexyl 2-cyano-3,3-diphenylacrylate and one or more dialkyl naphthalates, wherein the, wherein the 2-ethylhexyl 2-cyano-3,3-diphenylacrylate and the dialkyl naphthalates are present in a ratio of their respective weight percentages in the total formulation, of between about 0.03 to about 0.9 and the 2-ethylhexyl 2-cyano-3,3-diphenylacrylate comprises less than 3.5% of the formulation.

3. The cosmetic or dermatologic formulation of claim 1, wherein the 2-ethylhexyl 2-cyano-3,3-diphenylacrylate comprises less than 1% of the formulation.

4. The method of claim 2, wherein the 2-ethylhexyl 2-cyano-3,3-diphenylacrylate comprises less than 1% of the formulation.

* * * * *

UNITED STATES PATENT AND TRADEMARK OFFICE
CERTIFICATE OF CORRECTION

PATENT NO. : 6,491,901 B2
DATED : December 10, 2002
INVENTOR(S) : Heinrich Gers-Barlag et al.

It is certified that error appears in the above-identified patent and that said Letters Patent is hereby corrected as shown below:

Column 16,
Line 19, delete "wherein the, wherein the" to -- wherein the... --

Signed and Sealed this

Ninth Day of September, 2003

JAMES E. ROGAN
*Director of the United States Patent and Trademark Office*